(12) United States Patent  (10) Patent No.: US 8,226,574 B2
Whillock et al.  (45) Date of Patent: Jul. 24, 2012

(54) IMPAIRED SUBJECT DETECTION SYSTEM

(75) Inventors: Rand Whillock, North Oaks, MN (US); Isaac Cohen, Minnetonka, MN (US); Alexander Walsh, Los Angeles, CA (US)

(73) Assignee: Honeywell International Inc., Morristown, NJ (US)

( * ) Notice: Subject to any disclaimer, the term of this patent is extended or adjusted under 35 U.S.C. 154(b) by 1040 days.

(21) Appl. No.: 12/175,748

(22) Filed: Jul. 18, 2008

(65) Prior Publication Data

US 2010/0016754 A1 Jan. 21, 2010

(51) Int. Cl.
*A61B 13/00* (2006.01)
(52) U.S. Cl. .......................... 600/558; 351/210
(58) Field of Classification Search .................. 600/558; 351/210
See application file for complete search history.

(56) References Cited

U.S. PATENT DOCUMENTS

| | | | |
|---|---|---|---|
| 4,838,681 A * | 6/1989 | Pavlidis ........................ | 351/210 |
| 4,973,149 A | 11/1990 | Hutchinson | |
| 5,422,690 A | 6/1995 | Rothberg et al. | |
| 5,506,631 A | 4/1996 | Boothe et al. | |
| 5,555,895 A | 9/1996 | Ulmer et al. | |
| 5,668,622 A | 9/1997 | Charbonnier et al. | |
| 6,089,714 A | 7/2000 | Galiana et al. | |
| 6,702,757 B2 * | 3/2004 | Fukushima et al. ........... | 600/558 |
| 7,309,125 B2 | 12/2007 | Pugach et al. | |
| 7,309,315 B2 | 12/2007 | Kullok et al. | |
| 2005/0110950 A1 * | 5/2005 | Thorpe et al. .................. | 351/209 |
| 2007/0200663 A1 * | 8/2007 | White et al. .................. | 340/5.31 |
| 2008/0013047 A1 * | 1/2008 | Todd et al. ..................... | 351/203 |

* cited by examiner

*Primary Examiner* — Max Hindenburg
*Assistant Examiner* — Renee Danega
(74) *Attorney, Agent, or Firm* — Seager Tufte & Wickhem LLC

(57) ABSTRACT

A system for detecting abnormal eye movement in a subject to indicate possible impairment of the subject. The subject may be presented with a visual pattern to observe. The visual pattern may cause the subject's eyes to move. Images of the eye movements may be captured. An eye motion pattern may be computed from the images. The eye motion pattern may be classified relative to other eye motion patterns or a guide. The classification may indicate whether there appears to be an abnormal movement of the eye and thus an impairment of the subject. An identification of the subject may be obtained according to a biometric from the images and used to retrieve the subject's baseline eye motion pattern. A comparison of the computed eye motion pattern and the baseline eye motion pattern may indicate whether there is abnormal movement of the eye and thus an impairment of the subject.

14 Claims, 6 Drawing Sheets

IMPAIRED SUBJECT DETECTION SYSTEM

BACKGROUND

The present invention pertains to sobriety and drug test instrumentation. Particularly, the invention pertains to detection of eye movements, and more particularly of abnormal movements that indicate impairment of a subject.

SUMMARY

The invention is a system that presents a pattern to a subject to cause the subject to move its eyes from one position to another. A camera may capture images of the eye movement. The eye movement may be tracked, classified, compared, assessed and/or analyzed to determine whether there is an abnormality of the movement. The abnormality may indicate an impairment of the subject.

DESCRIPTION

Multiple applications may benefit from a system that can detect whether an individual is impaired due to alcohol, drugs or the like. An automated system that can determine whether an individual is fit for work or military duty may be useful for screening people for a wide range of high risk jobs and activities.

Law enforcement personnel may check a subject's eye motion as a field test for people driving under the influence of alcohol, drugs or the like. Law enforcement personnel may regularly use a horizontal gaze nystagmus test (HGN) for testing field sobriety. A test giver may look for nystagmus, which is an involuntary jerking of an eyeball. Horizontal gaze nystagmus may be seen when an impaired person tries to visually track an object having horizontal motion relative to the person. HGN may be especially apparent at the extreme ends of the visual tracking. Vertical gaze nystagmus (VGN) may also be used for like purposes. The test is similar to HGN except that the person may visually track an object having vertical motion. A variant of these tests, oblique gaze nystagmus (OGN), may include a person trying to visually track an object having various combinations of simultaneous horizontal and vertical motion. For the purposes of this discussion, gaze nystagmus (GN) tests include HGN, VGN and/or OGN tests.

The present invention is a system 10 designed to automatically perform a GN test using a video display and eye tracking mechanism. As an illustrative example of the invention herein may be a system 10 designed for HGN testing. A test, with a moving pattern shown on a visual pattern display 11 directed toward the person, may be used for any direction of GN testing.

Figure 1:
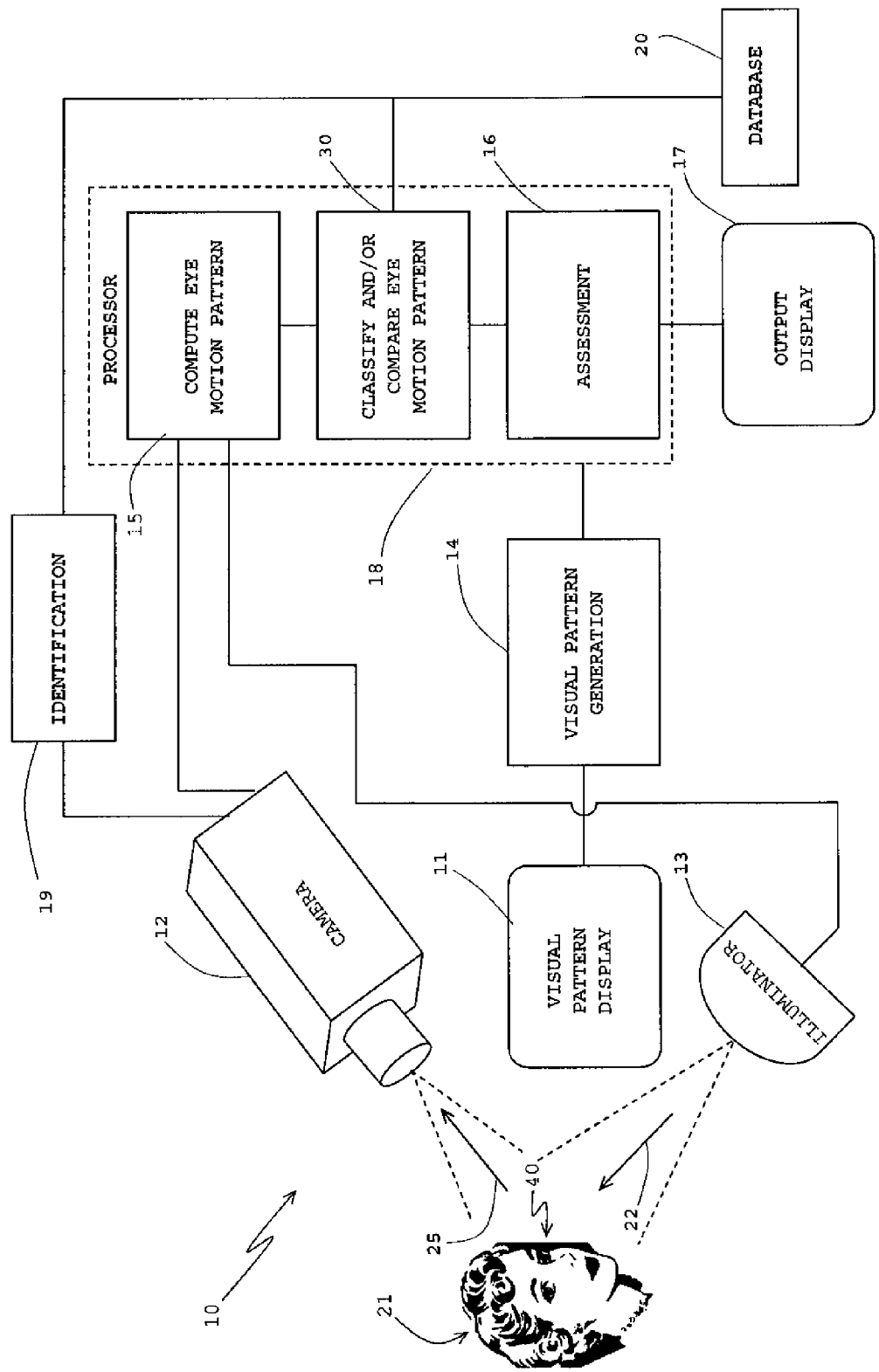
FIG. 1 is a diagram of the impaired subject detection system.

System 10 may use a video arrangement. The HGN test may be performed quickly with limited cooperation by the person being tested. FIG. 1 is a diagram of significant components of the system 10. The system may be referred to as an impaired subject detection system 10 (ISDS). Some of the components of the system may include a camera 12 and display 11 directed towards one or both eyes 40 of a person 21 (who may be regarded herein as also a subject 21) being tested. Also, an illuminator 13 may provide light 22, having a near-infrared wavelength, to provide illumination or to augment ambient illumination for better imaging with camera 12 of the subject's eyes 40. Illuminator 13 may provide light to the subject's eyes having wavelengths besides or instead of near infrared. Light 25 from subject 21 may reflect an image of the subject's eyes 40 to camera 12. Near-infrared light 22 from illuminator 13 should be relatively invisible to the human eye and thus not be a distraction to subject 21 being tested. During a test, subject 21 may look at a pattern display 11 while camera 12 takes a video or series of images of one or both eyes 40 of subject 21. Eye motion of subject 21 captured by camera 12, which is sensitive to near-infrared and possibly other wavelengths, may be in a form of a video or images conveyed to a compute eye motion pattern module 15. A computed eye motion pattern may go from module 15 to a classify and/or compare eye motion pattern module 30. Classification and/or comparison results may go to an assessment module 16. A processor 18 may contain modules 15, 30 and 16, and possibly other modules.

A key to performing an accurate GN test may be to have the subject's head remain somewhat steady while the subject is looking at and tracking with the eyes 40 a visual pattern in display 11. This may be accomplished in many ways including by varying the speed, pattern widths and/or pattern contrast of the pattern 23 presented in display 11. However, some movement of the subject's head may be compensated for by processor 18. Tracking of the visual pattern by the eyes may be revealed by a movement of the subject's eyes following one or more items in the pattern presented in display 11. Visual pattern display 11 may provide a specifically designed pattern providing a scene or items having motion to cause a subject to follow the motion with one or both eyes 40. The pattern may be provided to display 11 from a visual pattern generation module 14. Processor 18 may control the visual pattern generation module 14.

Figure 2:
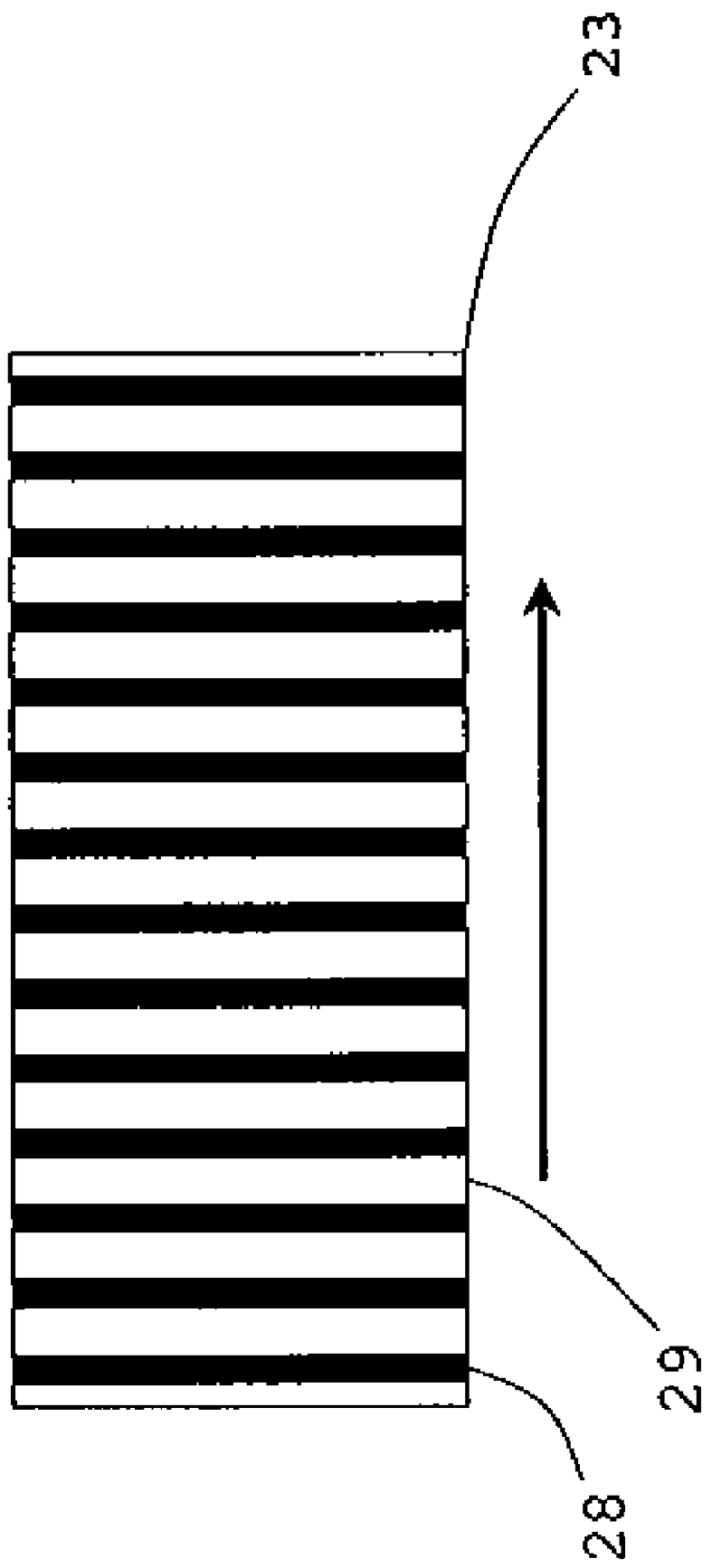
FIGS. 2 and 3 are illustrative examples of patterns which may be presented to initiate eye movement from the subject.

In FIG. 2, one illustrative example of a pattern in the display 11 may be a pattern 23 having high contrast vertical stripes (i.e., dark stripes 28 on a white background 29) moving from left to right when one looks towards the display 11. The direction of the stripes may be in another direction and/or be one of several different speeds. The bars may also be of various widths and contrast ratios such as grey on white or grey on black to elicit subtle impairments. Pattern 23 may mimic characteristics of an opticokinetic (OKN) drum that ophthalmologists might use to test certain eye functions including nystagmus.

Figure 3:
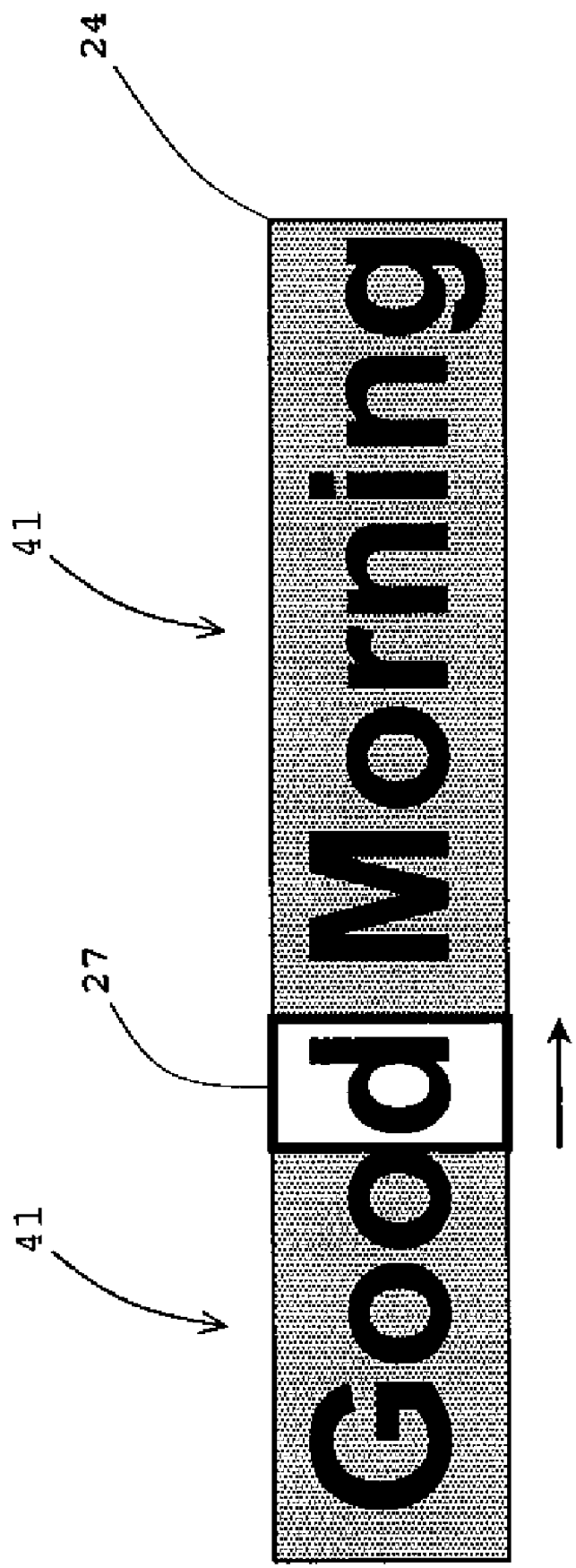

In FIG. 3, an alternative illustrative pattern 24 may include a left to right scrolling window 27 revealing a message 41 (e.g., "Good Morning"), one letter at a time, with the other letters of message 41 being momentarily obscured, for subject 21 to read. The test giver may request the subject to read the presented letters or the resulting message. Such request may inhibit the subject from evading the test or thwarting its results.

Figure 4:
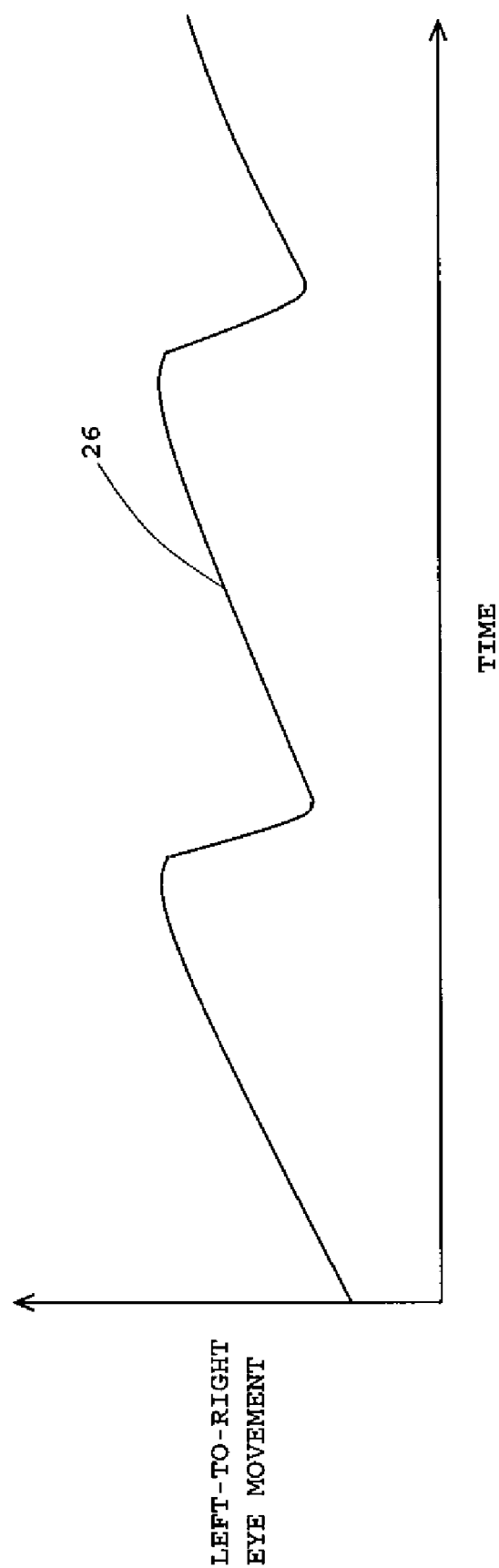
FIG. 4 is a graph of an illustrative example of non-normal eye movement.

As subject 21 watches the scrolling window 27 of pattern 24, or moving stripes 28 of pattern 23, on the display 11, the subject's eyes 40 may be imaged with a video camera 12. The captured video or images may be conveyed to the compute eye motion pattern module 15. Module 15 may compute an eye motion pattern. To detect the eye motion, module 15 may find the pupils from an eye or pupil feature, perhaps such as a glint of light off of a pupil, on the subject's eye or eyes 40 in each frame of the video or images or use a robust eye and iris detection algorithm. With a feature to lock on, then locations of a pupil may be plotted from frame to frame into a pupil movement track which may referred to as an eye motion track, an eye trajectory or an eye motion pattern. An illustrative example of an HGN eye motion pattern is shown with a curve 26 in a graph of FIG. 4. Curve 26 is plotted as left-to-right position of an eye 40 versus time in a direction looking towards an observed pattern 23 or 24. Curve 26 may be of other shapes for various instances of HGN plotting and/or of other subjects. Other visual patterns, including those for inducing various directions of eye movement, may be observed in plots, like curve 26, from tests using system 10.

A computed eye motion pattern from module 15 may be conveyed to a classify and/or compare eye motion pattern module 30. Classification results from module 30 may go to module 16 for determining an assessment, such as an impairment assessment of the subject 21.

An identification module 19 may be connected to camera 12 for identifying subject 21 based on image information, such as a biometric (e.g., face, iris recognition, or the like), from the camera. A biometric of subject 21 may be obtained for identification purposes and identification may be used to index a baseline eye motion pattern. A baseline eye motion pattern of an identified subject 21 may be retrieved from a database 20 and provided to module 30 for comparison with the computed eye motion pattern from module 15. Comparison results may go to assessment module 16 for determining an impairment assessment of subject 21.

Module 30 may classify and assess the eye motion pattern by comparing it to eye motion patterns having known normal and abnormal signatures, and to the baseline eye motion pattern of the subject. Classification of the eye motion pattern may alternatively be made according to a guide, look-up table, or the like. Comparison and/or classification of the eye motion pattern may in general indicate an impairment issue, if any, including the kind of impairment. Comparison of the eye motion pattern to the baseline eye motion pattern may indicate a condition specific to subject 21. That means that an apparent abnormal computed eye motion pattern from module 15 may appear normal when compared to the baseline eye motion pattern of subject 21. The various eye motion patterns may have corresponding mathematical descriptors.

Module 16 may perform an assessment of the eye motion pattern results from module 30 to detect specific features of impairment such as deviations from a smooth track that may point to nystagmus. For impaired individuals these deviations may be most noticeable, for example, at the end (right extreme) of the track for left to right movement induced by the pattern. The assessment module 16 may receive the results of the classification and/or comparison, and provide an assessment of the results to an operator at output display 17.

If the results of the test indicate an impairment of the subject, then a baseline of previous testing of the subject should be sought and noted. The baseline may reveal some already existing or inherent abnormality of eye movement in the subject 21. If so, then the amount of impairment indicated by module 16 of system 10 should be adjusted accordingly relative to the baseline.

Identification module 19 may provide biometric identification such as a face- or iris-based recognition. Module 19, connected to a database 20 and to module 30, may aid in identification of the subject and provide information for finding a baseline eye motion pattern of the subject for assessment of the computed eye motion patterns. Module 19 operations may be coordinated by processor 18, and module 19 may utilize the same camera 12 as used by the compute eye motion pattern module 15.

Results from module 16 may aid in identification of other issues, besides impairment, of subject 21. Other biometric or non-biometric identification approaches, may instead or in addition, be incorporated by identification module 19.

Figure 5A:
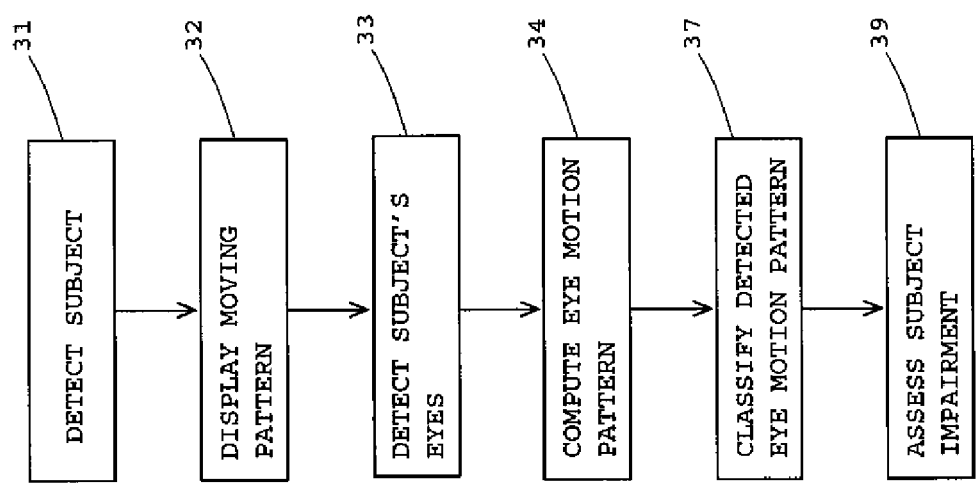
FIGS. 5a and 5b are flow diagrams of processes of the present system.

FIG. 5*a* shows a primary process flow for the impaired subject detection system 10. The process may relate to classification of eye motion patterns. After a subject 21 is detected in block or step 31; then in step 32, a moving visual pattern 23, 24, or other like-purpose visual pattern, may be presented on display 11 to that subject for viewing. System 10 may in step 33 detect the subject's eyes 40. In step 34, the system may detect motion of one or both eyes of the subject and compute the detected motion as an eye motion pattern. The computed eye motion pattern may be classified at step 37. After a classification of the computed eye motion pattern, then at step 39, the subject's impairment, if any, may be assessed. A message reporting results of system 10 may be displayed on output display 17.

Figure 5B:
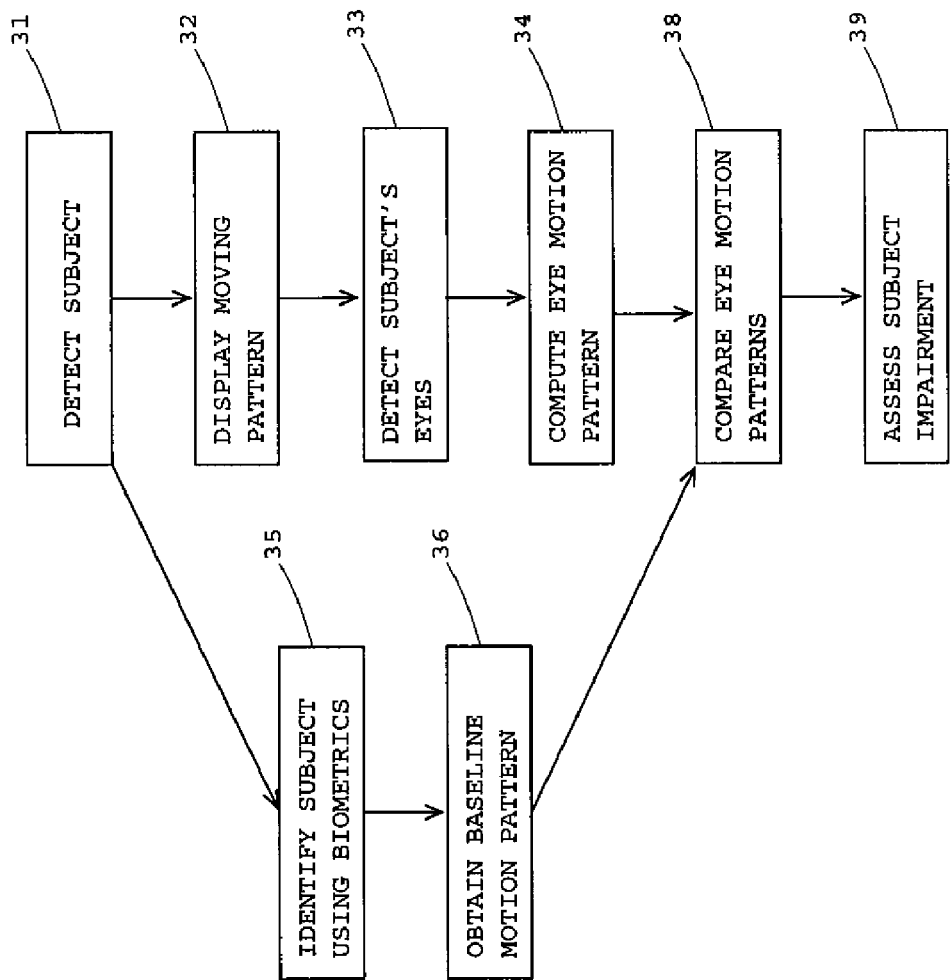

FIG. 5*b* shows a primary process flow for the impaired subject detection system 10. The process may relate to comparison of eye motion patterns. After a subject 21 is detected in block or step 31; then in step 32, a moving visual pattern 23, 24, or other like-purpose visual pattern, may be presented on display 11 to that subject for viewing. System 10 may in step 33 detect the subject's eyes 40. In step 34, the system may detect motion of one or both eyes of the subject and compute the detected motion as an eye motion pattern. In step 35, the subject may be identified using biometrics. With the identification, a baseline eye motion pattern for the subject may be obtained at step 36. At step 38, the computed eye motion pattern from step 34 may be compared with the baseline eye motion pattern from step 36. After the comparison in step 38, the subject's impairment, if any, may be assessed at step 39. A message reporting results of system 10 may be displayed on output display 17. System 10 may also be used for analyses and assessments of eye motion patterns for various purposes other than for detecting and assessing impairment of a subject.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. An impaired subject detection system comprising:
a camera for capturing images of an eye or eyes of a subject viewing a visual pattern;
a visual pattern generation module for generating the visual pattern, wherein the visual pattern includes a scrolling window that reveals a message essentially one letter at a time, with other letters of the message obscured, the visual pattern being designed to cause a movement of an eye or eyes of the subject viewing the visual pattern via a display;
an eye motion pattern computation module connected to the camera; and
an assessment module connected to the eye motion pattern computation module.

2. The system of claim 1, wherein the assessment module is for indicating whether the movement of the eye or eyes reveals an impairment of the subject.

3. The system of claim 2, wherein the eye motion pattern computation module is for computing an eye motion pattern of the movement of the eye or eyes.

4. The system of claim 3, further comprising:
an identification module connected to the camera;
a classify and/or compare eye motion pattern module connected to the eye motion pattern computation module and the assessment module; and
a database module connected to the identification module and the classify and/or compare eye motion pattern module.

5. The system of claim 4 wherein:
the identification module is for identifying the subject;
the database module is for providing a baseline eye motion pattern of the subject or a mathematical descriptor of the baseline eye motion pattern;
the classify and/or compare eye motion pattern module is for receiving the eye motion pattern from the eye motion computation module, classifying the eye motion pattern and/or comparing the eye motion pattern or its mathematical descriptor with the baseline eye motion pattern or its mathematical descriptor; and
the assessment module is for receiving results of the classifying and/or comparing from the classify and/or compare eye motion pattern module and determining a likelihood and/or a degree of impairment of the subject from the results.

6. The system of claim 5, wherein:
the identification module is for determining an identity of the subject based on a biometric in one or more images from the camera; and
the visual pattern is for providing a gaze nystagmus test.

7. The system of claim 6, further comprising:
an illuminator for illuminating the eye or eyes of the subject with light; and
wherein the light comprises a near infrared wavelength; and
the camera is sensitive to near infrared light.

8. A method for detecting a temporarily impaired subject comprising:
providing a display of a moving pattern for a subject to view;
capturing images of an eye or eyes of the subject observing the moving pattern;
measuring motion of the eye or eyes from the images;
computing an eye motion pattern of the motion of the eye or eyes from the images;
classifying the eye motion pattern or its mathematical descriptor according to a classification guide for eye motion patterns or their mathematical descriptors;
comparing the eye motion pattern, or its mathematical descriptor, with a baseline eye motion pattern, or its mathematical descriptor, of the subject; and
assessing an amount of impairment, if any, of the subject according to the comparing.

9. The method of claim 8, wherein:
the impairment is indicated by gaze nystagmus of the motion of the eye or eyes of the subject; and
an amount of impairment is indicative of a sobriety of the subject.

10. The method of claim 8, comprising illuminating the eye or eyes with near infrared light.

11. The method of claim 8, wherein:
forming an eye motion pattern of the motion of the eye or eyes from the images; and
using a biometric from one or more of the images to identify the subject from a biometric database; and
comparing the eye motion pattern or its mathematical descriptor with a baseline eye motion pattern or its mathematical descriptor for the subject from the database.

12. A system for detecting and analyzing eye movements of a subject, comprising:
a biometric identification module for identifying a subject;
a database for providing baseline eye motion patterns of identified subjects;
a display for the subject to observe at least one moving item;
a camera for capturing images of an eye or eyes of the subject; and
a processor, connected to the camera, for measuring motion or tracking movement of the eye or eyes as revealed in the images, and for evaluating the movement of the eye or eyes to determine an amount of impairment, if any, of the subject;
wherein:
the movement of an eye is formatted as an eye motion pattern; and
the eye motion pattern is compared with a baseline eye motion pattern of the identified subject from the database to assess the amount of impairment of the subject.

13. The system of claim 12, wherein the processor is for compensating a result relative to a movement of a head of the subject.

14. The system of claim 12, wherein
the impairment is a gaze nystagmus; and
the impairment is indicative of sobriety of the subject.

* * * * *